United States Patent [19]

Allen et al.

[11] Patent Number: 4,987,085

[45] Date of Patent: Jan. 22, 1991

[54] BLOOD FILTERING METERING DEVICE

[75] Inventors: Michael P. Allen, Sunnyvale; Urs A. Ramel, Portola Valley; Anthony J. DeLizza, Sunnyvale, all of Calif.

[73] Assignee: Chemtrak Inc., Sunnyvale, Calif.

[21] Appl. No.: 324,407

[22] Filed: Mar. 16, 1989

Related U.S. Application Data

[63] Continuation-in-part of Ser. No. 195,881, May 19, 1988, and a continuation-in-part of Ser. No. 64,883, Jun. 22, 1987.

[51] Int. Cl.$^5$ .................. G01N 21/00; G01N 21/77; G01N 31/22
[52] U.S. Cl. .................... 436/169; 436/170; 422/56; 422/57; 422/58; 422/61
[58] Field of Search .............. 436/169, 170; 422/58, 422/57, 56, 61

[56] References Cited

U.S. PATENT DOCUMENTS

| | | | |
|---|---|---|---|
| 3,511,608 | 5/1970 | Anderson | 422/56 |
| 4,477,575 | 10/1984 | Vogel et al. | |
| 4,604,264 | 8/1986 | Rothe et al. | 422/57 |
| 4,738,823 | 4/1988 | Engelmann | 422/56 |
| 4,774,192 | 9/1988 | Terminiello | |
| 4,839,297 | 6/1989 | Freitag et al. | 436/170 |
| 4,876,067 | 10/1989 | Deneke et al. | 436/169 |

FOREIGN PATENT DOCUMENTS 2222951 7/1974 Fed. Rep. of Germany .

Primary Examiner—Robert J. Warden
Assistant Examiner—Thalia P. Vassilatos
Attorney, Agent, or Firm—Bertram I. Rowland

[57] ABSTRACT

Constructions are provided for removing interfering red blood cells from a blood sample and providing a measured amount of serum or plasma to a pad. The pad serves as a bridge for the transfer of reagent between two bibulous strips, resulting in transfer of reagent solution through the pad and transport of a material to be measured to the measuring region of the strips. Particularly, glass fiber membranes are used in conjunction with cellulosic membranes to minimize red blood cell lysis, remove red blood cells and provide a measured amount of sample.

20 Claims, 2 Drawing Sheets

BLOOD FILTERING METERING DEVICE

CROSS-REFERENCE TO RELATED APPLICATIONS

This application is a continuation-in-part of application Ser. No. 195,881, filed May 19, 1988 and 064,883, filed June 22, 1987, which disclosures are incorporated herein by reference in their entirety.

INTRODUCTION

1. Technical Field

The field of the subject invention concerns diagnostic assay strips permitting visual measurement and providing for red blood cell free fluid from blood.

1. Background

The ability to measure a wide variety of physiologically active compounds, both naturally occurring and synthetic, has become of increasing importance, both as an adjunct to diagnosis and therapy. While for the most part, assays of physiological fluids and drugs have required clinical laboratory determinations, there is an increasing awareness of the importance of being able to carry out assay determinations in the doctor's office and in the home. To be able to perform an assay in a doctor's office or home requires that an assay have a simple protocol and be relatively free of sensitivity to small changes in the conditions under which the assay is carried out. Importantly, inaccurate measurements of reagents and sample should whenever feasible be avoided. Numerous systems have been developed in efforts to try to address the various problems associated with analysis outside of the clinical laboratory. There is, nevertheless, a continuing interest in providing improved and alternative methods to those which are presently generally available.

Exemplary of this situation is the need today to be able to determine cholesterol levels or low or high density lipoprotein levels in blood. There is a clearly established relationship between total blood cholesterol (mainly LDL fraction) and coronary artery disease (Journal of the American Medical Association (1985) 253:2080–2086). New guidelines have been established for adults over 20 years of age to identify risk groups associated with blood cholesterol level. These levels are as follows: <200 mg/dl is a desirable blood cholesterol; 239 mg/dl is borderline high blood cholesterol; >240 mg/dl is high blood cholesterol.

Cholesterol levels can be controlled by both diet and cholesterol lowering drugs. The key is to identify those individuals at risk. Being able to monitor one's own cholesterol at home for those individuals at risk will provide a significant tool in monitoring cholesterol levels and reducing the potential for heart disease. The measuring of other naturally occurring compounds of physiologic importance and synthetic drugs is also of great interest.

In many of the assays it will be necessary to provide a blood sample free of red blood cells to a measurement strip. Furthermore, for home use or use by non-technical individuals, it will be desirable that the volume of sample applied to a measurement strip permit a relatively broad range of sample volume, which is then accurately metered to the measuring strip. Any such device must be relatively simple, provide reproducible results, and be in a form which allows it to be joined to a measurement strip in a fixed or removable manner.

Relevant Literature

Demacker et al., *Clin. Chem.* (1983) 29:1916–1922 reports the evaluation of cholesterol assay kits. Studies associated with enzyme assays include Gochman and Schmitz, *Clin. Chem.* (1971) 17:12; Paul, *The Enzymes* (1963) 8:227–274; *Current Status of Blood Cholesterol Measurement in Clinical Laboratories in the United States: A Report from the Laboratory Standardization Panel of the National Cholesterol Education Program* (1988) 34(1):193–201; and U.S. Pat. Nos. 4,391,904; 4,366,241; 4,168,146; 4,435,504; 4,533,629; 4,540,659, and references cited therein.

German Pat. No. 22 22 951 describes a filter assembly containing chemical reagents for removing cells from blood and measuring CPK.

SUMMARY OF THE INVENTION

Novel constructions are provided which efficiently remove red blood cells from a blood sample while metering a reproducible volume to a measuring strip. The construction is removable from the measuring strip for assaying an analyte in the blood sample.

DESCRIPTION OF THE SPECIFIC EMBODIMENTS

Figure 1A:
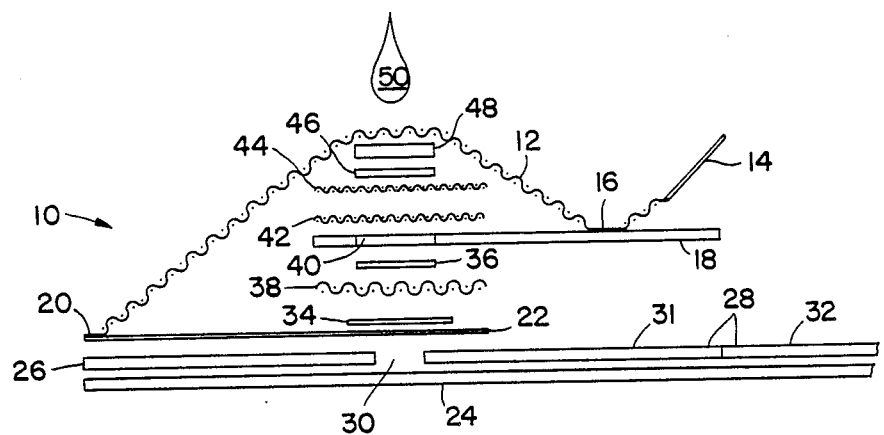
FIGS. 1a and b are diagrammatic side elevational cross-sections of a device according to this invention with 1a being an exploded view of 1b.

Methods and apparatus are provided for the detection of analytes employing a removable multi-layered composite for the removal of interfering cells from blood and metering a predetermined volume to a measuring strip. The composite involves a multiplicity of fluid transferring layers which in the direction of movement through the composite device removes interfering red blood cells, feeding the resulting plasma to a metering layer combination. A removable metering layer combination provides a predetermined volume to the measurement strip. In a particular embodiment, the volume is present on the reaction pad.

The sample may be presented to the device as a drop, a series of drops, or the like. The layers through which the sample flows will include a mesh layer, a first membrane, and a second membrane cooperating with the first membrane to ensure the substantially complete removal of any interfering cells from the blood sample. The red blood cell free plasma or serum is then transported to a metering means. Means employed include a reagent pad which communicates with an absorption reservoir through a perforated plastic layer which acts as a barrier for liquid transmission until the reagent pad is saturated or a mesh layer which can act to remove superfluous fluid from the pad.

The first cellular separation member is used to reduce the concentration of red and white blood cells received by the second filtration member. By lowering the red blood cell content from about 10 to 90%, usually from about 30% to 90% of the original red blood cell content, with the first membrane member, the second membrane member is able to efficiently and accurately remove at least substantially all of the red blood cells from the blood sample. Since the first membrane acts as a coarse separation means, the first membrane may take any of a wide variety of forms.

Various packings or sieving depth filters may be employed, such as glass fibers, cellulose filters treated with red blood cell capture reagents, glass fiber filters, or synthetic fiber filters. Glass fiber filters are available from such manufacturers as Whatman, Schleicher and Schuell, MSI, and Pall. The glass fiber filters are further characterized by a glass fiber diameter in the range of about 0.5–9 $\mu$, and a density of about 50 to 150 g/m$^2$. The glass fiber filters may be illustrated by S&S Glass 30, Whatman GFD, and S&S 3662.

Other coarse separation membranes may include cellulosic membranes, e.g. filter paper, to which red blood cell binding proteins or agglutination agents immobilized. Such proteins may include lectins, antibodies specific for RBC surface membrane proteins, thrombin, ion exchange agents, etc. The preparation of such filters by conjugating proteins or other agents to cellulose is well known. Cellulose may be activated in a wide variety of ways employing carbodiimide, carbonyl diimidazole, cyanogen bromide, chloroacetic acid, where the acid may then be activated with carbodiimide, or the like. The literature is replete with examples of binding of proteins to cellulosic membranes for a variety of reasons, which techniques may be employed here. Alternatively, multiple layers of course separation membranes may be employed.

With the two membranes, immediately beneath the first membrane will be the second membrane, which will be in fluid receiving relationship with the first membrane, either in contact with the first membrane or in close proximity thereto. Generally, the spacing between the first and second membranes will not exceed a distance which inhibits fluid flow, so that fluid readily flows from the first to the second membrane. The non-asymmetric membranes which are employed will be those in the medium porosity range, having an average porosity in the range of about 0.65 $\mu$ to 7 $\mu$, preferably about 1 to 5 $\mu$, where the pores may or may not be of substantially uniform diameter through the membrane. By contrast, where an asymmetric membrane is employed, that is the diameter of the pores vary from one surface to the other, desirably the membrane will have a minimum porosity not less than about 0.4 $\mu$, preferably not less than about 0.45 $\mu$, and the maximum porosity will generally not exceed about 40 $\mu$, more usually not exceed about 20 $\mu$. Illustrative microporous membranes which may find use include Filterite polysulfone asymmetric, 20 $\mu$ –0.45 $\mu$, Sartorious cellulose acetate, 1.2 $\mu$, Nucleopore, etc.

The choice of the second membrane is important, since the amount of red blood cell lysis is dependent on a number of factors. Depending on the size of the pores, the amount of lysis will greatly vary. Since lysis results in release of colored cell components, which interfere with detection of the border in the measuring strip and act to decompose hydrogen peroxide, merely removing cells is insufficient. A further consideration is the pressure differential across the membranes. Again, the appropriate choice of membranes will affect the pressure drop and forces acting on the cells, where the pressure differential can affect the stability of the cells.

Thus, the two membranes serve to act together to efficiently and accurately remove red blood cells from the blood sample with little, if any, hemolysis, so as to provide a plasma or serum sample which may be accurately analyzed without interference from hemolytic products, such as heme.

The plasma or serum from the second membrane is received by the reactant pad component of the metering device, which is normally impregnated with at least one reagent for reaction with a component of the plasma received from the second membrane. The reactant pad will be a bibulous member able to absorb the fluid received from the second membrane. Various bibulous materials may be used, such as cellulosic materials, e.g., paper, or the like. The reactant pad will usually be of a size in the range of 5 to 50 mm$^2$ surface area and a thickness in the range of about 0.1 to 2 mm, having a volume capacity of from about 1 to 30 $\mu$l. The reactant pad may be round, square, rectangular, quadrilateral or polygonal, depending on the manner in which it is to be used to act as a bridge for the measuring strips. For further characterization see application Ser. No. 195,881, filed May 19, 1988.

Various metering systems may be employed to insure the substantial reproducibility of the amount of fluid sample absorbed by the reactant pad. The systems may involve absorbant pads separated by a substantially non-wettable mesh or a film which serves to wipe away excess sample from the reactant pad.

The first embodiment comprises a perforated plastic barrier, where the plastic is not readily wettable so as to prevent flow of plasma until the reactant pad is saturated. The barrier may be a screen having a mesh from about 100 $\mu$m to about 1 mm, preferably from about 200 $\mu$m to about 500 $\mu$m. The thickness will generally be from about 150 $\mu$m to 600 $\mu$m, more usually from about 200 $\mu$m to 400 $\mu$m. Alternatively, a film of similar thickness may be utilized by having one or a few holes of from about 0.05 to 2 mm in diameter. The holes must be large enough and appropriately spaced to allow for the pad to act as a fluid transfer bridge with the absorbant pad. The composition may be nylon, polyester, polyethylene or the like, so long as the dimensions and composition do not allow continuity of capillary flow between the reactant pad and the absorption layer, but allows for wicking upon saturation of the reactant pad.

The particular nature of the absorbant pad is not critical to the invention, serving to absorb overflow of the sample from the reactant pad. Depending on the anticipated size of the sample, the absorbant pad will be large enough to accommodate the overflow. Usually, the absorbant pad will have a volume of from about 1 to 60 $\mu$l and a thickness of from about 0.1 to 5 mm. The absorbant pad will be affixed or seated on an inert film which will separate the absorbant pad from the measuring strip. In this way none of the sample can reach the measuring strip until the film is removed. When the film is removed, typically the absorbant pad is removed with it and the reactant pad is brought into liquid transferring contact with the measuring strip.

A second embodiment employs a mesh screen in contact with the reactant pad. The mesh screen can be moved in the direction normal to the measuring strip, so that it may act as a squeegee to remove superfluous fluid from the reactant pad. A film underneath the mesh screen prevents any sample from contacting the measuring strip. A fine mesh material may be used as the wiping element, such as Nitec, having pores of from about 100 to 350 $\mu$.

The filtering and metering device is provided as a removable composite of a plurality of layers.

In one embodiment, to allow for removal, a flexible mesh screen is provided which covers the first membrane and extends on opposite sides of the first membrane, being attached at one end to an inert support film, supporting the absorbant pad, and proximal to the other end to a second support backing which supports the second membrane on one side and to which the reactant pad is bound on the other side. The supporting layer is attached to the measuring strip device, so as to bring the reactant pad into contact with the measuring strip. This will become clearer as the construction of the device and the drawings are considered. The end of the flexible mesh extends away from the second support, so that after saturation of the reactant pad, the layers other than the reactant pad and its support may be removed by pulling at the extended end of the mesh.

The sample receiving first membrane is bound underneath and to the mesh, so as to be positioned over the other layers. Various adhering methods may be employed to adhere the first membrane to the mesh. The first membrane may be a circular or rectangular pad or have any convenient shape which allows for flow of the sample through the first membrane while inhibiting loss of sample. Various adhesives may be employed to firmly bind the first membrane to the mesh, conveniently at the edges of the first membrane. Beneath the first membrane and mounted on an inert solid support is the second membrane. The solid support is a thin rigid or flexible film, generally of a thickness in the range of about 0.002 inch to 0.025 inch. Conveniently, the film may be made of Mylar, PVA, PVC, or the like. This film will be attached to the measuring strip device by any convenient means, such as spot welding to the measuring strip device support film, adhesive at the edges, or the like. The particular manner of bonding is not critical, so long as the bonding does not interfere with the assay. The support may extend over the measuring strip, partially or substantially completely enclosing the measuring strip comprising the measuring zone, acting as a protective barrier. For the most part, the support strip will be clear, particularly if it extends over the measuring zone.

Beneath the second membrane is an opening which allows insertion or placing of the reactant pad for transfer of the sample to the reactant pad. Within the opening and held fixed by the perforated film is the reactant pad. Any convenient method for adhering or securing the pad to the support may be employed. Convenient methods for adhering the pad include adhesion or compression. The reactant pad is in contact with the perforated film, which is in contact with the absorbant layer, so as to allow for transfer of liquid from the reactant pad through the barrier layer to the absorbant pad. The barrier layer acts as a directional membrane in allowing flow in only one direction. Thus, when the overflow from the reactant pad is absorbed by the absorbant pad, fluid contact is broken with the reactant pad and there is no further flow to the absorbant pad. The absorbant pad is supported by an inert unperforated film support which is removable along with the mesh screen. This support extends away from the absorbant layer, normally toward the end of the strip which serves to receive various liquids. Conveniently, the support film for the second membrane extends in the direction of the flow of the liquids toward the measurement region of the strip.

The mesh can be bonded at one end to the support for the absorbant layer, extend over and beyond the first membrane, be bound to the second support prior to its end and allow the extension to serve as a pull tab for removing the composite construction prior to carrying out the wicking assay and subsequent to the reactant pad receiving the sample. While a mesh is particularly convenient, a mesh is not required, since a film with an appropriately situated orifice will also suffice. However, the mesh does provide a rough filtration and will serve to remove any particulate matter which may be in the sample, protecting the first membrane from clogging.

In another embodiment, two unconnected pulls are used, where the first pull is bonded to a plastic film to which is bound a mesh, the two membranes and a third membrane as appropriate. The second pull removes the wiping film and the underlying protective film.

The subject device provides particular use with the device described in U.S. application Ser. No. 064,883, filed June 22, 1987 and application Ser. No. 195,881, filed May 19, 1988.

The subject method may be employed in any situation where a fixed amount of a substance is involved, which can be transferred to the reactant pad for measurement or further reaction and reacts with another compound to produce a detectable boundary. These types of assays may be illustrated by ELISA assays, EMIT assays, sandwich assays, or the like.

Depending upon the protocol, the reactant pad to which the sample is added may be prepared in a variety of ways. It may be untreated, impregnated with buffer, or provide a reagent signal-producing system. A variety of sophisticated reagents, protocols or regimens can be devised based on a limited amount of material migrating to produce a boundary in proportion to the amount of material present. Examples of protocols would include particles having first and second ligands, where the first ligand competes with analyte for receptor bound to a surface. After carrying out the competition for a limited amount of receptor between analyte and particle, an aliquot of the assay medium is transferred to the sample pad and the particle transported with effluent through the measurement region. By having receptor for the second ligand in the measurement region, the particle boundary will be defined by the number of particles added to the pad. By having colored particles, charcoal particles, magnetic particles, dyes, dye-polymer conjugates, proteins with high visible extinction coefficients, e.g. phycobiliproteins, or the like, the boundary will be readily defined.

Any technique which allows for binding of a detectable entity in proportion to an analyte of interest may be employed. These may include cleavage of a bond to release the entity, where the bond to the entity is not cleavable when the entity is bound to a receptor, binding to a support which inhibits migration of the entity in proportion to the amount of analyte in a sample, or the like. The entity may be a particle as described above, an enzyme which catalyzes the production of a detectable product, or the like.

Of particular interest is where a product is produced on the sample pad which provides for a detectable boundary. For example, where the analyte is a substrate, the sample pad may be impregnated with the appropriate enzyme or enzymes to provide for a product. Normally, the enzyme product will react, either directly or indirectly, with a compound which is fixed in the assay measurement region. This may be exemplified by cholesterol, glucose, or the like, which reacts with an oxidase to provide an oxidizing species. The oxidizing species may then react with the bound compound or a mobile compound which reacts with the bound compound, to produce a detectable boundary. Illustrative of this situation would be the hydrolysis of serum cholesterol ester by cholesterol esterase (EC:3.1.1.13) and subsequent oxidation of cholesterol by cholesterol oxidase (EC:1.1.3.6) to produce a stoichiometrically identical amount of $H_2O_2$. This $H_2O_2$ is formed at a stationary reaction pad and combines with horseradish peroxidase (HRP) which is in the mobile phase. The HRP·$H_2O_2$ reacts with a bound substrate to produce a detectable boundary.

Depending upon the assay, other reagents may also be present. For example, detergents find use where a lipophilic analyte in blood is involved, where the lipophilic analyte binds to proteins present in the blood. This may be illustrated by cholesterol which binds to proteins, as for example in very low, low, and high density lipoproteins. Thus, detergents such as non-ionic, anionic, or cationic detergents may be employed. Of particular interest are polyoxyalkylenes, ethoxylated alkylphenols, octylphenoxypolyethoxyethanol, octylphenol-ethylene oxide condensates and polyoxyethylene lauryl ethers, or anionic detergents, such as bile acids, e.g., sodium cholate and sodium taurocholate. In addition, various sticking agents or adhesives may be employed, such as gum arabic. Also of interest will be proteins which are substantially noninterfering, which may include gelatin, casein, serum albumin, or gamma globulins. In addition, the reagent pad may include preservatives, such as sucrose, polyvinyl alcohol, polyvinyl pyrrolidone, dextran or sodium azide. Finally, a buffered solution will normally be employed for impregnating the pad, where any convenient buffer may be employed, generally a substantially dilute buffer, which may include phosphate, tris, MOPS, borate, carbonate, or the like. Usually, the buffered solution will be at a pH in the range of about 4 to 9. The buffer concentration will generally be from about 10 to 500 mM.

In the case of the cholesterol assay as illustrative of other assays, the impregnating solution will have from about 2 to 100 units/ml of the two enzymes, cholesterol esterase and cholesterol oxidase. The detergents will be in total weight from about 0.1 to 5 weight percent of the medium, while in the case of mixtures the weight of the non-ionic detergents may be from about 10% to 90%, usually from about 25 to 75 weight percent of the total detergent mixture. The binding agents or adhesives will generally be in the range of about 0.2 to 10, more usually from about 1 to 5 weight percent of the medium. A preservative or hydrogen bonding agent may be present in from about 1 to 20 weight percent, more usually from about 2 to 10 weight percent. The remaining additives will generally be present in total amount of less than about 10 weight percent, more usually of less than about 5 weight percent. The remaining composition may be water, non-reactive ingredients, excipients, extenders, and the like.

The assay is carried out by impregnating a reactant pad which serves as a bridge between two bibulous members positioned in tandem juxtaposition along their long axes. Thus the two strips define one long strip with a separation between the two strips, where the reactant pad can act as a bridge to allow fluid flow between the two strips. A first bibulous member serves to receive the transport solution, which may or may not have reaction components, depending upon the assay. The first bibulous member transfers the fluid to the reactant pad. The second bibulous member receives the transport fluid from the reactant pad and serves as a bridge to transfer the transport fluid from the reactant pad to the assay measurement region. The sample is prevented from interacting with the two bibulous members when sample is transferred to the pad by a separation means, usually an inert non-porous film, which blocks transfer from the reactant pad to the bibulous members. The amount of sample accepted by the reactant pad and involved in the assay medium may be controlled by providing for transfer of fluid beyond the amount saturating the pad through a non-wetting screen into an absorbant layer. After addition of the sample to the reactant pad, and an incubation of up to about 30 minutes, the porous non-wetting material and absorbant layer are removed, leaving the reactant pad as the sole repository of sample for the assay. Where the wiping film is employed it will be removed upon saturation of the reactant pad.

The entire strip may have a length of about 25 to 200 mm, more usually from about 50 to 150 mm, preferably about 100 mm. About 25% to 90% of the length of the strip will be the measurement or quantitation area. The strips which provide for flow of fluid to and from the reactant pad may be of the same or different length and will generally be from about 5 to 25 mm, more usually about 10% to 20% each of the length of the strip. The reactant pad will generally be from about 1% to 10%, more usually from about 2% to 8% of the length of the strip; the longer the strip, the larger the reactant pad may normally be. The width of the strip may be varied widely, usually being at least about 2 mm and not more than about 10 mm, preferably from about 3 to 7 mm. The two strips will usually each overlap the reactant pad by at least about 0.2 mm and not more than about 2 mm, usually about 1 mm, being primarily a matter of convenience, so long as the two strips are not in direct fluid communication.

Any convenient material may be used for the various bibulous parts of the assay strip. Usually, the thickness of the bibulous components will be in the range of about 0.05 to 2.0 mm, more usually 0.15 to 0.75 mm. A wide variety of bibulous supports may be employed, particularly cellulosic supports, such as chromatography paper, silica on a support, alumina on a support, and polymeric membranes such as nitrocellulose and nylon. The characteristics of the bibulous material employed for the measurement region or zone include the need in many instances to covalently or irreversibly bind an indicator molecule to the support, that the color developed should be clear and sharp, and that the fluid should be capable of flowing at a convenient rate through the bibulous member. In addition, the bibulous member should be able to adhere to a support, as well as allowing for adherence of the bridging bibulous member, the reactant pad, to the measurement region bibulous member without significant interference with flow from the bridging member to the measurement member.

The support layer may be any convenient rigid backing material, generally from about 0.002 to about 0.1 inch, more usually from about 0.005 to 0.025 inch thick. A wide variety of rigid convenient materials are available, for the most part polymers, which include polystyrene, polyvinylacetate, polyvinylchloride, polyester, etc. The adhesive layer may be any convenient adhesive which does not significantly penetrate the bibulous member and interfere with flow. For the most part, double-stick tape adhesive has been found to be convenient and successful. Double-stick adhesives include 3M 415, 443, or 9460.

For further understanding of the invention, the drawings will now be considered.

In FIGS. 1a and b is depicted the assay device 10, comprising a mesh sheet 12 with pull tab 14. The mesh sheet 12 is temporarily adhered at position 16 to plastic sheet 18 and permanently at position 20 to plastic strip 22. In this way, when pull tab 14 is pulled, mesh sheet 12 releases at position 16 removing plastic strip 22 and other components adhering thereto from assay device 10.

The assay device has a rigid backing 24. Mounted on the backing 24 are reagent receiving strips 26 and quantitation strips 28 separated by space 30. Quantitation strip 28 has transfer zone 31 and quantitation zone 32. The plastic strip 22 rests on the strips 26 and 28 and supports the absorbant pad 34. Overlying and separating absorbant pad 34 from reactant pad 36 is non-wettable mesh 38, bound to plastic strip 18, maintaining reactant pad 36 in opening 40. Reactant pad 36 fits in opening 40 of plastic sheet 18. Final filtration membranes 42 and 44 are placed over the reactant pad 36, with filtration membrane 42 mounted on plastic strip 18, positioning the reactant pad 36 in opening 40 and filtration membrane 44 affixed to mesh 12 to be removed when mesh 12 is stripped from the device. Two glass fiber membranes 46 and 48 complete the device and serve to remove substantially all of the red blood cells from blood drop 50, which passes through the membranes and filters until absorbed by reactant pad 36 and absorbant pad 34. Once the absorbant pad 34 is saturated, pull tab 14 is pulled whereby mesh 12 and plastic strip 22 are pulled out, along with membranes 46 and 48, filter 44 and absorbant pad 34, leaving reactant pad 36 in fluid communication with bridging reagent receiving strip 26 and quantitation strip 28.

Figure 2A:
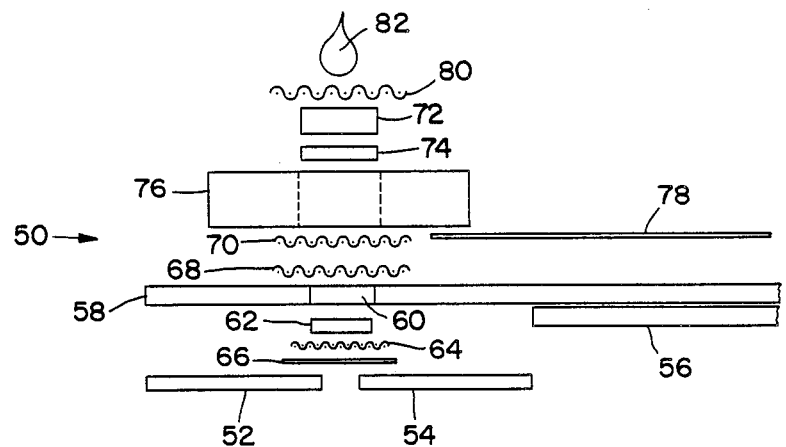
FIGS. 2a and b are an alternative embodiment of the invention and are diagrammatic side elevational cross-sections of a device.

The device depicted in FIGS. 2a and b comprises a reagent receiving strip 52, a transfer zone strip 54 and a quantitation strip 56 mounted under a rigid plastic support sheet 58 having hole 60 for receiving reactant pad 62. Underlying reactant pad 62 is a squeegee mesh 64 which extends normally to support sheet 58 and can be pulled out from under support sheet 58. Affixed to squeegee mesh 64 is a plastic strip 66 which prevents sample from reaching strips 52 and 54 until removed. Two final filtration membranes 68 and 70 serve to capture any cell debris which escapes from first and second fiberglass membranes 72 and 74, respectively. The fiberglass membranes 72 and 74 are fitted into plastic holder 60 76 affixed to pull tab 78 at one end. Seated on plastic holder 76 is mesh 80 serving as a coarse filter. Blood drop 82 is placed on mesh 80, where the blood drop migrates downwardly by gravity and capillary action through the filters to be absorbed by reactant pad 62. Excess sample collects in squeegee mesh 64, when the squeegee mesh 64 is pulled out it wipes the reactant pad and takes excess sample with it. The plastic strip 66 affixed to squeegee mesh 64 is also removed bringing reactant pad 62 in contact with the underlying strips 52 and 54. Also, pull tab is removed removing the membranes 72 and 74, holder 76 and filter 70.

The assay may then be initated by dipping reagent receiving strip 52 into a reagent solution, whereby the solution migrates through the reagent receiving strip 52 and the reactant pad 62 where it carries the mobile components of the assay system from the reactant pad 62 through transfer strip 54 to quantitation strip 56. The reaction of a component from the reactant pad 62 with a reactant on the quantitation strip 56 results in a detectable color. The distance of the color from the pad is related to the amount of analyte in the sample.

Figure 1B:

A construction was made substantially as described in FIG. 1 excluding the metering components. A microporous membrane (Filterite polysulfone asymmetric, 20 $\mu$ –0.45 $\mu$, or Sartorious cellulose acetate 1.2 $\mu$, Nucleopore or a nylon mesh screen (Nitex, 3-325-58) were laminated to two Mylar members, spaced apart, to leave an opening over the membrane. A 3×5 mm gap between the Mylar film was provided with the membrane or screen side down, glass fiber filters were layered above the gap. Immediately above the gap was a 3×5 mm piece of S&S glass 30, upon which was placed a 7×5 mm piece of Whatman GF/D (GF=glass fiber) fiber filter. The total water absorbance capacity of the filters in this configuration is 42 $\mu$L. The filters were held in place with 3M booktape (Scotch 845), joining the upper filter and each Mylar member.

The complete assembly was situated in contact with a 5×5 mm S&S paper filter on a plexiglass board, so that the membrane contacted the paper. The assembly was held fast with a nylon mesh screen.

Blood of known hematocrit (30%) was applied to the device through the mesh with a variable positive displacement pipet. The blood was allowed to filter for 1 min. 40 sec. before the device was removed from the paper pad. The pad was then weighed and its hemoglobin content measured with detergent extraction in a pseudo peroxidase assay.

The results are summarized in the following Table 1. The membrane devices provided better quality serum than the nylon mesh device. The nylon mesh did not participate in cell filtration.

TABLE 1

| | | RECOVERY OF SERUM FROM FILTRATION | | | | | |
|---|---|---|---|---|---|---|---|
| Applied Blood Volume | % Serum Volume To GF Capacity | Gradient Membrane Filterite Membrane | | 1.2$\mu$ Membrane | | Nylon Mesh (no membrane) | |
| | | Volume | Hb | Volume | Hb | Volume | Hb |
| 30 $\mu$L | 50% | 4.8 $\mu$l | .33 mg/mL | 3.2 $\mu$l | .18 mg/mL | 4.6, 3.8 $\mu$l | 9.0, 3.9 mg/mL |
| 40 $\mu$L | 66% | 5.5 $\mu$l | .32 mg/mL | 6.1 $\mu$l | .34 mg/mL | 10.3, 9.85 $\mu$l | 17.1, 35.5 mg/mL |
| 50 $\mu$L | 82% | 9.4 $\mu$l | .42 mg/mL | 9.8 $\mu$l | .40 mg/mL | 12.5, 11.7 $\mu$l | 16.4, 49 mg/mL |

In the next study the quantitation of the volume absorbed by the past was investigated.

METERING DATA

1. Threshold Metering (Table 2)

A reagent pad was situated above a mesh screen and an absorbent pad. Increasing volumes of human plasma were added (6, 7, 8, 9, 10, 12, 15$\mu$L) to the reagent pad. The retained plasma, after metering, was quantitated by weighing the wet reagent pad. The dry weight was taken as an average for the size pad, and the weight difference between the wet pad and dry pad taken to be demonstrative of the plasma fill volume.

TABLE 2

THRESHOLD METERING

| Sample Size μL | Dry Wt. gms | Wet Wt. gms | Rec. Vol μL | Metered |
|---|---|---|---|---|
| 1 | 6 | .0030 | .0090 | 6.0 | No |
| 2 | 6 | .0030 | .0090 | 6.0 | No |
| 3 | 6 | .0030 | .0091 | 6.1 | No |
| 4 | 7 | .0030 | .0087 | 5.7 | ? |
| 5 | 7 | .0030 | .0086 | 5.6 | ? |
| 6 | 7 | .0030 | .0084 | 5.4 | ? |
| 7 | 8 | .0030 | .0082 | 5.2 | Yes |
| 8 | 8 | .0030 | .0080 | 5.0 | Yes |
| 9 | 8 | .0030 | .0080 | 5.0 | Yes |
| 10 | 9 | .0030 | .0080 | 5.0 | Yes |
| 11 | 9 | .0030 | .0082 | 5.2 | Yes |
| 12 | 9 | .0030 | .0078 | 4.8 | Yes |
| 13 | 10 | .0030 | .0081 | 5.1 | Yes |
| 14 | 10 | .0030 | .0082 | 5.2 | Yes |
| 15 | 10 | .0030 | .0079 | 4.9 | Yes |
| 16 | 12 | .0030 | .0082 | 5.2 | Yes |
| 17 | 12 | .0030 | .0081 | 5.1 | Yes |
| 18 | 12 | .0030 | .0079 | 4.9 | Yes |
| 19 | 15 | .0030 | .0082 | 5.2 | Yes |

2. Wipe Away Metering (Table 3)

Figure 2B:
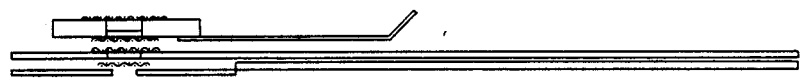

A reagent pad was situated in a device similar in construction to that described in FIG. 2, with the reagent pad positioned within a confined space in a plastic assembly with a mesh screen on a plastic sheet in contact on the effluent side. Liquid plasma was added to the top of the reagent pad in increasing increments (6, 7, 9, 12, 15 and 20μL) and the excess removed by pulling the screen on a plastic strip across the pad after wetting and removing the strip. The wet reagent was weighed and the weight different taken to represent the liquid fill.

TABLE 3

WIPE AWAY METERING DATA ON PLASMA SAMPLE

| | Sample Size μL | Recov. Vol. μL |
|---|---|---|
| 1 | 6 | 5.3 |
| 2 | 6 | 5.2 |
| 3 | 6 | 5.1 |
| 4 | 6 | 5.3 |
| 5 | 6 | 5.2 |
| 6 | 7 | 5.2 |
| 7 | 7 | 5.4 |
| 8 | 7 | 5.5 |
| 9 | 7 | 5.4 |
| 10 | 7 | 5.5 |
| 11 | 9 | 5.4 |
| 12 | 9 | 5.1 |
| 13 | 9 | 5.1 |
| 14 | 9 | 5.2 |
| 15 | 9 | 5.4 |
| 16 | 12 | 5.3 |
| 17 | 12 | 5.3 |
| 18 | 12 | 5.4 |
| 19 | 12 | 5.5 |
| 20 | 12 | 5.2 |
| 21 | 15 | 5.6 |
| 22 | 15 | 5.1 |
| 23 | 15 | 5.2 |
| 24 | 15 | 5.4 |
| 25 | 15 | 5.5 |
| 26 | 20 | 5.6 |
| 27 | 20 | 5.5 |
| 28 | 20 | 5.3 |
| 29 | 20 | 5.3 |
| 30 | 20 | 5.1 |

It is evident from the above results, that a convenient construction is provided which serves to remove interfering cells, particularly red blood cells, from blood, allows for accurate measurement of a volume, without requiring premeasurement, and minimizes lysis of red blood cells which may interfere with the assay determination. In addition, the construction may be removed from the assay strip, leaving a pad which serves as a bridge between a first portion of the assay strip which is in position to receive reagent and the second extended portion of the assay strip which is used for the measurement. Thus, the reagents flow through the metering pad to ensure that all of the sample is contacted with the developing reagents.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device for separating cells from blood to produce plasma and metering a predetermined amount of plasma to a reactant pad without significant red blood cell lysis, said device comprising:
   a filtering system of descending pore size to provide for successive removal of red blood cells without significant red blood cell lysis;
   a reactant pad for receiving said plasma sample from said filtering system; and
   removable means for removing overflow sample from contact with said reactant pad.

2. A device according to claim 1, wherein said means for removing overflow sample comprises a non-wettable mesh in contact with and underneath said reactant pad and an absorbant pad in contact with the side of said mesh opposite said reactant pad.

3. A device according to claim 1, wherein said means for removing overflow sample comprises a movable mesh in contact with the bottom of said reactant pad for receiving sample overflow and wiping the bottom of said reactant pad when moved.

4. A device for separating cells from blood to produce plasma and metering a predetermined amount of plasma to a reactant pad without significant red blood cell lysis, said device comprising:
   a first coarse filter to remove from about 10% to 90% of the red blood cells in a blood sample;
   a second fine filter to remove substantially all of the remaining red blood cells in said sample to provide a plasma sample;
   a reactant pad for receiving said plasma sample from said second fine filter;
   a perforated barrier below said reactant pad to prevent plasma flow until said reactant pad is saturated and to interrupt flow once said overflow has been absorbed; and
   an absorbent pad to receive plasma from said reactant pad upon overflow after saturation of said reactant pad.

5. A device according to claim 4, including an inert perforated support between said second fine filter and said reactant pad; an inert unperforated support under said absorbent pad; and a perforated film contacting said inert perforated support and said unperforated support and under said first coarse filter for separating said perforated film, said unperforated support and said absorbent pad from said reactant pad.

6. A device according to claim 5, wherein said barrier is a plastic mesh.

7. A device according to claim 5, wherein said barrier is a plastic perforated film.

8. A device according to claim 5, wherein said film is a plastic mesh.

9. A device according to claim 8, wherein said barrier is a plastic mesh.

10. A device according to claim 8, wherein said barrier is a plastic perforated film.

11. A device according to claim 5, including an assay device comprising:
   a bibulous member support film;
   first and second bibulous members supported by said support film in tandem separated juxtaposition along their long axes, positioned under said reactant pad, so that upon removal of said unperforated film, said reactant pad acts as a bridge between said first and second bibulous members; and
   said perforated support is bonded to said bibulous member support film to urge said reactant pad in fluid transferring relationship with said bibulous strips upon removal of said unperforated support.

12. A device according to claim 11, wherein said fine filter has pores of substantially uniform diameter in the range of about 0.65 to 7 $\mu$.

13. A device according to claim 11, wherein said fine filter has asymmetric pores.

14. A device according to claim 11, wherein said filters are glass fiber filters.

15. A device for measuring an analyte in a blood sample involving separating cells from blood to produce plasma and metering a predetermined amount of plasma to a reactant pad without significant red blood cell lysis, said device comprising:
   a filtering and metering device comprising:
   a plastic mesh;
   a first coarse filter to remove from about 10% to 90% of the red blood cells in a blood sample;
   a second fine filter to remove substantially all of the remaining red blood cells in said sample to provide a plasma sample;
   a reactant pad for receiving said plasma sample from said second fine filter;
   a perforated barrier to prevent plasma flow until said reactant pad is saturated and to interrupt flow once said overflow has been absorbed; and
   an absorbent pad to receive plasma from said reactant pad upon overflow after saturation of said reactant pad;
   wherein said plastic mesh is bonded to said unperforated barrier and said coarse filter is reversibly bonded to said perforated barrier, whereby on pulling said mesh, said mesh, unperforated barrier and coarse filter are separated from said reactant pad and perforated barrier;
   an assay device comprising:
   a bibulous member support film;
   first and second bibulous members supported by said support film in tandem separated juxtaposition along their long axes, positioned under said reactant pad, so that upon removal of said unperforated film, said reactant pad acts as a bridge between said first and second bibulous members; and
   said perforated support is bonded to said bibulous member support film to urge said reactant pad in fluid transferring relationship with said bibulous strips upon removal of said unperforated support.

16. A device for separating cells from blood to produce plasma and metering a predetermined amount of plasma to a reactant pad without significant red blood cell lysis, said device comprising:
   a first coarse filter to remove from about 10% to 90% of the red blood cells in a blood sample;
   a second fine filter to remove substantially all of the remaining red blood cells in said sample to provide a plasma sample;
   a reactant pad for receiving said plasma sample from said second fine filter;
   a movable mesh film in contact with and underneath said pad for receiving overflow and wiping the bottom of said pad when moved.

17. A device for measuring an analyte in a blood sample involving separating cells from blood to produce plasma and metering a predetermined amount of plasma to a reactant pad without significant red blood cell lysis, said device comprising:
   a filtering and metering device comprising:
   a first coarse filter to remove from about 10% to 90% of the red blood cells in a blood sample;
   a second fine filter to remove substantially all of the remaining red blood cells in said sample to provide a plasma sample;
   a pull tab having an opening in which said first and second filters are fitted;
   a reactant pad for receiving said plasma sample from said second fine filter;
   a movable mesh underneath and incontact with said pad for receiving overflow sample and wiping said pad when moved; and
   an unperforated film underneath and affixed to said movable mesh to prevent sample from passing; and
   an assay device comprising:
   a bibulous member support film;
   first and second bibulous members supported by said support film in tandem separated juxtaposition along their long axes, positioned under said reactant pad, so that upon removal of said unperforated film, said reactant pad acts as a bridge between said first and second bibulous members.

18. A device according to claim 17, wherein said fine filter has pores of substantially uniform diameter in the range of about 0.65 to 7 $\mu$.

19. A device according to claim 17, wherein said fine filter has asymmetric pores.

20. A device according to claim 17, wherein said filters are glass fiber filters.

* * * * *

UNITED STATES PATENT AND TRADEMARK OFFICE
CERTIFICATE OF CORRECTION

PATENT NO. : 4,987,085

DATED : January 22, 1991

INVENTOR(S) : MICHAEL P. ALLEN; URS A. RAMEL; ANTHONY J. DeLIZZA

It is certified that error appears in the above-identified patent and that said Letters Patent is hereby corrected as shown below:

On title page, item [63] delete the reference to Serial No. 64,883.

Col. 1, lines 7-9 delete:

"and 064,883, filed June 22, 1987, which disclosures are incorporated herein by reference in their entirety" and insert: --which disclosure is incorporated herein by reference in its entirety--.

Signed and Sealed this

Twenty-fifth Day of April, 1995

Attest:

BRUCE LEHMAN

*Attesting Officer*     Commissioner of Patents and Trademarks